(12) United States Patent
Yoo et al.

(10) Patent No.: US 9,516,113 B2
(45) Date of Patent: Dec. 6, 2016

(54) APPARATUS, METHOD AND SERVER FOR PROVIDING CONTENT

(71) Applicant: HYUNDAI MNSOFT, Inc., Seoul (KR)

(72) Inventors: Young Soo Yoo, Seoul (KR); Sang Won Yang, Seoul (KR)

(73) Assignee: HYUNDAI MNSOFT, INC., Seoul (KR)

( * ) Notice: Subject to any disclaimer, the term of this patent is extended or adjusted under 35 U.S.C. 154(b) by 230 days.

(21) Appl. No.: 14/067,078

(22) Filed: Oct. 30, 2013

(65) Prior Publication Data

US 2015/0006617 A1 Jan. 1, 2015

(30) Foreign Application Priority Data

Jun. 28, 2013 (KR) ........................ 10-2013-0075054

(51) Int. Cl.
*G06F 15/16* (2006.01)
*H04L 29/08* (2006.01)
(Continued)

(52) U.S. Cl.
CPC ............ *H04L 67/12* (2013.01); *A61B 5/0022* (2013.01); *A61B 5/02055* (2013.01); *A61B 5/1112* (2013.01); *A61B 5/1118* (2013.01); *G01C 21/20* (2013.01); *H04M 1/72522* (2013.01); *A61B 5/024* (2013.01); *A61B 5/0816* (2013.01); *A61B 5/1123* (2013.01); *A61B 5/4809* (2013.01); *A63B 2230/06* (2013.01); *A63B 2230/42* (2013.01); *A63B 2230/50* (2013.01); *H04M 2250/10* (2013.01); *H04M 2250/12* (2013.01)

(58) Field of Classification Search
CPC ............ H04L 67/12; H04M 2250/10; H04M 2250/12; A61B 5/0022; A61B 5/02055; A61B 5/1112–5/1118; A61B 5/1123; A61B 5/024
USPC ................................ 709/203, 201, 204, 205
See application file for complete search history.

(56) References Cited

U.S. PATENT DOCUMENTS

| 2004/0103139 | A1* | 5/2004 | Hubbard | ............ G06Q 30/0212 709/201 |
| 2009/0262206 | A1* | 10/2009 | Park | ................. G08B 13/19641 348/218.1 |
| 2012/0084349 | A1* | 4/2012 | Lee | ........................ G06Q 30/02 709/203 |

(Continued)

FOREIGN PATENT DOCUMENTS

KR 10-2012-0136974 12/2012

*Primary Examiner* — Thu Ha Nguyen
(74) *Attorney, Agent, or Firm* — Bacon & Thomas, PLLC

(57) ABSTRACT

A method for providing content includes transmitting to the content providing server a user's location detection signal; receiving the user's location detection signal from the content providing apparatus; transmitting a user's activity recognition signal; receiving the user's activity recognition signal; transmitting a user's bio-signal; receiving the user's bio-signal; determining a user's status based on the user's location detection signal and the user's activity recognition signal. Further, the method includes estimating a user's biological activity based on the determined user's location and the user's bio-signal; transmitting the content corresponding to the user's biological activity; receiving the content corresponding to the user's biological activity from the content providing server; and providing the received content.

13 Claims, 3 Drawing Sheets

(51) Int. Cl.
*G01C 21/20* (2006.01)
*A61B 5/00* (2006.01)
*A61B 5/0205* (2006.01)
*H04M 1/725* (2006.01)
*A61B 5/11* (2006.01)
*A61B 5/024* (2006.01)
*A61B 5/08* (2006.01)

(56) References Cited

U.S. PATENT DOCUMENTS

| | | | | |
|---|---|---|---|---|
| 2012/0117020 A1* | 5/2012 | Davis | ................... | G06F 19/345 706/54 |
| 2012/0239507 A1* | 9/2012 | Braginsky | .............. | G06Q 10/10 705/14.69 |
| 2013/0110565 A1* | 5/2013 | Means, Jr. | ........... | G06Q 10/063 705/7.11 |
| 2013/0212168 A1* | 8/2013 | Bonasera | ............ | G06F 19/3418 709/203 |
| 2014/0095420 A1* | 4/2014 | Chun | ..................... | G06Q 50/24 706/46 |
| 2014/0266939 A1* | 9/2014 | Baringer | ................. | H01Q 21/28 343/729 |
| 2014/0275850 A1* | 9/2014 | Venkatraman | ....... | A61B 5/0002 600/301 |
| 2014/0278229 A1* | 9/2014 | Hong | ................... | A61B 5/7455 702/160 |
| 2014/0288435 A1* | 9/2014 | Richards | ............ | A61B 5/02427 600/479 |
| 2015/0186609 A1* | 7/2015 | Utter, II | .............. | A61B 5/0022 600/301 |
| 2016/0057565 A1* | 2/2016 | Gold | ...................... | H04W 4/008 455/41.1 |
| 2016/0154952 A1* | 6/2016 | Venkatraman | .......... | G06F 21/32 705/44 |
| 2016/0166197 A1* | 6/2016 | Venkatraman | ......... | A61B 5/486 600/301 |

* cited by examiner

APPARATUS, METHOD AND SERVER FOR PROVIDING CONTENT

CROSS-REFERENCE TO RELATED APPLICATION(S)

The present invention claims priority of Korean Patent Application No. 10-2013-0075054, filed on Jun. 28, 2013, which is incorporated herein by reference.

FIELD OF THE INVENTION

The present invention relates to a content providing apparatus, a content providing method and a content providing server. More particularly, the present invention relates to an apparatus, method and server for providing content, capable of actively providing a user with a variety of content by analyzing a user's behavior and determining location and condition of a user.

BACKGROUND OF THE INVENTION

Generally, a navigation system mounted on, e.g., a vehicle, captures its current location based on location information of the vehicle received through GPS (Global Positioning System) satellites, reads data of a current location from a road database which is built therein or wirelessly received from the outside, and displays the road together with the location of the vehicle, thereby helping the user to identify the location of a currently driving road or to find a destination with ease when driving on the first trip.

In order to satisfy user needs, in recent years, a user is provided with more precise route information through advanced technologies, which are integrated into a navigation system or a smart phone, such as informing expected arrival time from a starting point to a destination and suggesting a detour depending on a road situation to the destination, when a user sets the destination.

As such, in a technology to guide a route to a destination, the technology is becoming highly developed to satisfy user needs.

Related art of the disclosure is disclosed in Korean Laid-Open patent No. 10-2012-0136974 "CONTENT PROVIDING SYSTEM AND A PROVIDING METHOD THEREOF FOR EFFECTIVELY DISTRIBUTING CONTENT USE COSTS TO VARIOUS RIGHT PERSONS RELATED TO CONTENT," published on Dec. 2, 2012.

Furthermore, recently, a new technical trend is included in navigation systems or smartphones to provide a variety of content such as music or movies to a user as well as to guide a route to a destination through navigation systems or smartphones.

However, there exists an inconvenience that a user has to directly operate a navigation system to select his or her desired content so that the user enjoys the content through the navigation system. In addition, limited kinds of content hinder the feeling of a user's satisfaction.

SUMMARY OF THE INVENTION

In view of the above, the present invention provides an apparatus, method and server for providing content, capable of actively providing a user with a variety of content by analyzing a user's behavior and determining location and condition of a user.

In accordance with a first aspect of the present invention, there is provided a method for providing content that is executed by a content providing apparatus including a location detection unit and an activity recognition unit, a content providing server including a controller or a bio-signal sensing unit which is integrally formed with the content providing apparatus or is incorporated in separate devices. The method includes the content providing apparatus transmitting to the content providing server a user's location detection signal detected by a location detection unit; the content providing server receiving the user's location detection signal from the content providing apparatus; the content providing apparatus transmitting to the content providing server a user's activity recognition signal recognized by an activity recognition unit; the content providing server receiving the user's activity recognition signal from the content providing apparatus; the content providing apparatus transmitting a user's bio-signal received from the bio-signal sensing unit to the content providing server; the content providing server receiving the user's bio-signal from the content providing apparatus or the bio-signal sensing unit; the controller determining a user's status based on the user's location detection signal and the user's activity recognition signal; the controller estimating a user's biological activity based on the determined user's location and the user's bio-signal; the content providing server transmitting the content corresponding to the user's biological activity which is estimated based on at least one of a user's location determined using the user's status determined based on the user's location detection signal and the user's activity recognition signal, and the user's bio-signal to the content providing apparatus; the content providing apparatus receiving the content corresponding to the user's biological activity from the content providing server; and the content providing apparatus providing the received content.

Further, the transmitting a bio-signal to the content providing server may comprise transmitting any one of bio-signals including a heart rate, a body temperature and a breathe period to the content providing server.

Further, the estimating a biological activity of the user may comprise estimating the biological activity of the user using at least one of bio-signals including a heart rate, body temperature, and breath period.

The method may further comprise, when it is determined that the user is indoors or when it is estimated that the biological activity of the user is sleeping, determining whether a destination and an expected arrival time are set; and when it is determined that the destination and the estimated arrival time are set, transmitting content including at least one of route information to reach the destination, traffic information and weather information in the course of moving to the destination to the content providing apparatus.

The method may further comprise, when it is determined that the user is indoors or when it is estimated that the biological activity of the user is sleeping, transmitting content including at least one of route information to reach a destination within an expected arrival time, traffic information containing a public transport, and a departure time.

The method may further comprise, when it is estimated that the biological activity of the user is walking on foot or riding on a car, determining whether a destination and an expected arrival time are set; and when it is determined that the destination and the expected arrival time are set, transmitting content including at least one of route information to reach the destination within the expected arrival time and traffic information about a public transport to reach the destination to the content providing apparatus.

The method may further comprise, when it is estimated that the biological activity of the user is one of running, riding a bike, or climbing a mountain, transmitting the content providing apparatus content including health information, route information and calorie consumption information to the content providing apparatus, wherein the route information includes a moving speed and location of the earlier of the user.

The method may further comprise, when it is estimated that the biological activity of the user is climbing a mountain, transmitting content including route information relating to a shelter located near a mountain trail, in consideration of an expected descent time of the user depending on weather of the day to the content providing apparatus.

Further, the transmitting content to the content providing apparatus may comprise transmitting at least one of content including health information, weather information, route information, traffic information, news information, and advertisements to the content providing apparatus.

In accordance with a second aspect of the present invention, there is provided an apparatus for providing content. The apparatus includes a location detection unit configured to detect a location of a user to produce a location detection signal; an activity recognition configured to recognize an activity of the user to produce an activity recognition signal; a communication unit configured to transmit the location detection signal and the activity recognition signal, receive a bio-signal from a bio-signal sensing unit, and receive content from the content providing server; and a display unit configured to represent the content.

Further, the communication unit may be further configured to any one of bio-signals comprising heart rate, body temperature and breathe period to the content providing server.

Further, the content apparatus may comprise one of a navigation system or a smartphone.

Further, the content providing apparatus may further comprise a separate display unit, wherein the separate display unit comprises any one of wearable glasses or a wearable watch.

Further, the glasses may be configured to represent the content through a left lens or a right lens of the glasses in accordance with a predetermined condition.

Further, the glasses may be configured to represent the content on an upper, lower, left, or right section of left or right lenses thereof.

In accordance with a third aspect of the present invention, there is provided a server of providing content. The server includes an additional communication unit configured to receive a user's location detection signal, a user's activity recognition signal and a user's biological activity signal; a memory unit configured to store content to be provided to the content providing apparatus; and a controller configured to determine a user's status based on the user's location detection signal and the user's activity recognition signal, estimate a user's biological activity based on a user's location determined using the determined user's status and the bio-signal, and extract content corresponding to the estimated user's biological activity from the memory unit to provide the extracted content to the content providing apparatus through the additional communication unit.

Further, the controller may estimate the biological activity of the user based on any one of bio-signals including a heart rate, a body temperature, and a breath period.

Further, the controller may transmit at least one content of health information, weather information, route information, traffic information, news information, and advertisements to the content providing apparatus.

The content providing apparatus and server in accordance with the embodiments of the present invention detect a user's location and biological activity, determine a user's correct location and actively provide content suitable for the user, thereby increasing a user's convenience and enhancing a feeling of satisfaction.

BRIEF DESCRIPTION OF THE DRAWINGS

The above and other objects and features of the present invention will become apparent from the following description of the embodiments given in conjunction with the accompanying drawings, in which.

DETAILED DESCRIPTION OF THE EMBODIMENTS

Figure 1:
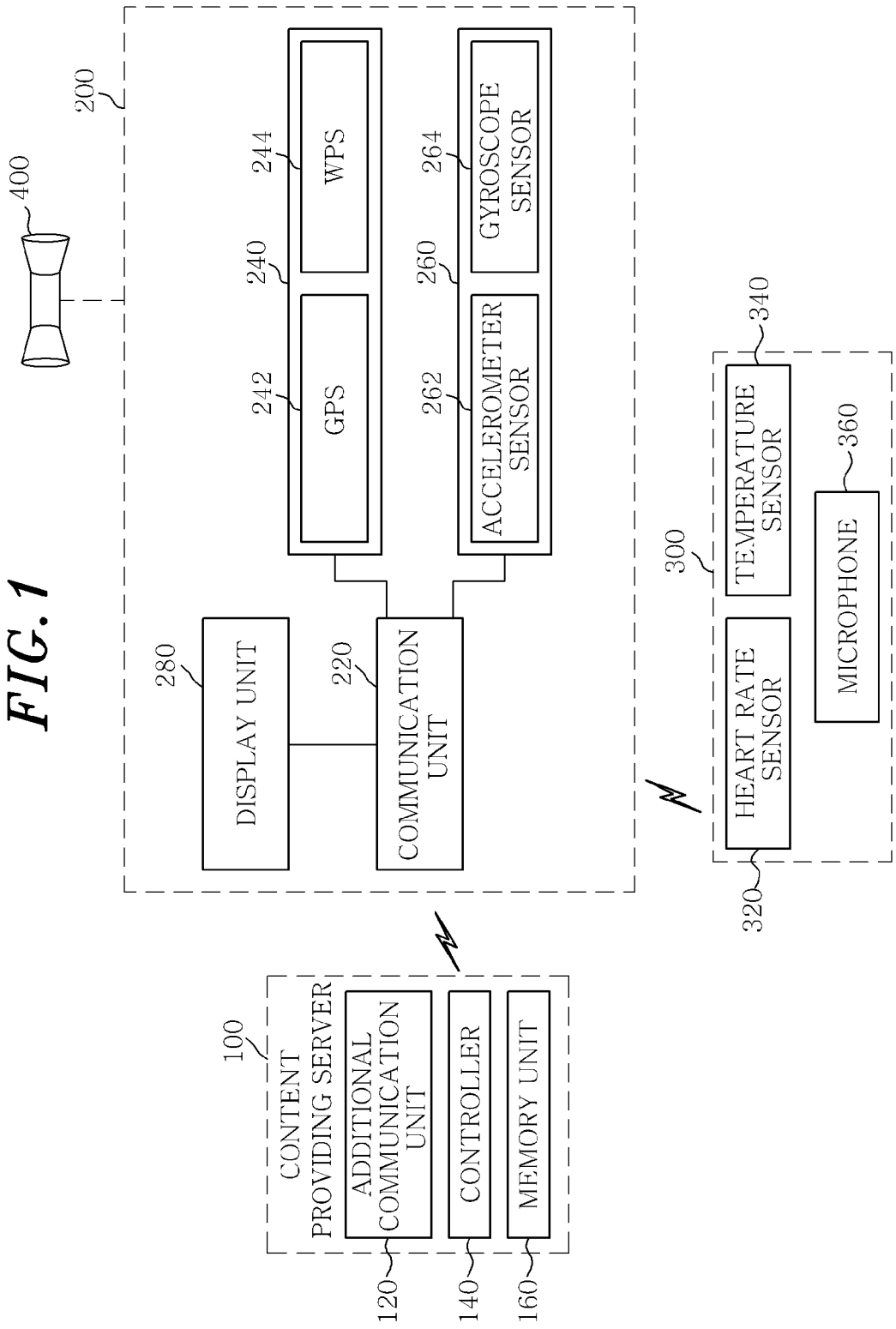
FIG. 1 is a functional block diagram of an apparatus and a server for providing content in accordance with an embodiment of the present invention.

Hereinafter, a route guiding apparatus, a route guiding server and a route guiding method in accordance with an embodiment of the present invention will be described in detail with reference to the accompanying drawings. In the drawings, thickness of lines and size of components shown in the drawings may be exaggerated for the purpose of descriptive clarity and for the sake of convenience. Further, the following terms are defined in consideration of the functions of the present invention, which may vary depending on intensions of a user or an operator or practices. Therefore, the definition of such terms should be made on the basis of the disclosure throughout the present specification FIG. 1 is a functional block diagram of an apparatus and a server for providing content in accordance with an embodiment of the present invention.

As illustrated in FIG. 1, a content providing apparatus 200 in accordance with an embodiment of the present invention includes a communication unit 220, a location detection unit 240, an activity recognition unit 260 and a display unit 280.

The communication unit 220 transmits to the content provider server 100 a user's location detection signal detected by the location detection unit 240 and a user's activity recognition signal recognized by the activity recognition unit 260, receives a user's bio-signal from the bio-signal sensing unit 300, and receives content corresponding to a user's location and the bio-signal from the content provider server 100.

The bio-signal sensing unit 300 is responsible for sensing bio-signals. Especially, the bio-signal sensing unit 300 of the embodiment includes a heart rate sensor 320, a temperature sensor 340 and a microphone 360 and collects the bio-signals such as a heart rate, a body temperature and a breath period from the respective components.

In accordance with the embodiment, the bio-signal sensing unit 300 may be incorporated in a device such as user's glasses or a watch, which is wearable on a user, in order to make a correct bio-signal sensing of a user, but not limited thereto. Alternatively, the bio-signal sensing unit 300 may be integrally formed with the content providing apparatus 200.

The location detection unit 240 serves to receive coordinate information and detect a location of a user. Especially, the location detection unit 240 detects a location of the user who holds the content providing apparatus 200 and includes a GPS (Global Positioning System) 242 and a WPS (WiFi-based Positioning System) 244.

To put it more specific, the GPS 242 receives coordinate information from one or more of GPS satellites 400, and the WPS 244 receives information of a wireless AP (Access Point) inputted thereto to detect the user's location.

In the case where a user is located indoors, signal strength of the GPS 242 is relatively weaker than that of the WPS 244. In contrast, in the case where a user is located outdoors, signal strength of the GPS 242 is relatively stronger than that of the WPS 244.

Accordingly, the content provider server 100, which will be described later, may determine a location of an outdoor user based on information provided from the GPS 242, and a location of an indoor user based on information provided from the WPS 244.

The activity recognition unit 260 is used to recognize a user's activity. Especially, the activity recognition unit 260 includes an accelerometer sensor 262 to sense a user's acceleration and/or a gyroscope sensor 264 to sense a user's rotational inertia and recognizes an operation of a user who holds the content providing apparatus 200.

The display unit 280 represents to the user the content received through the communication unit 220.

In accordance with the embodiments, the content providing apparatus 200 may provide with its own controller (not shown) and render the controller to integrally control the location detection unit 240, an activity recognition unit 260 and a display unit 280.

In addition, a route to a destination is not guided necessarily through the display unit 280 included in the content providing apparatus 200. Accordingly, it may be possible to display the route to the destination onto the glasses and/or the watch which may contain the bio-signal sensing unit 300.

That is, the embodiment of the present invention may be configured to deliver the content, which is received by the communication unit 220 from the content providing server the content providing server 100, to the glasses or the watch, so that the user can enjoy the content represented through even a separate display resource including the glasses or the watch.

Especially, where the content received from the content providing server 100 is routing information to a destination, the routing information may be transmitted to the glasses or the watch as route guidance information in the form of TBT (Turn By Turn).

Actually, the glasses or the watch itself may play a role of the content providing apparatus 200, and if so, the content received through the communication unit 220 may be represented through diverse display resource.

By way of example, it is possible to configure a display scheme in such a manner that the content may be represented through a left lens or a right lens in accordance with a predetermined condition. Further, it is also possible to represent the content on upper, lower, left, or right section of the left or right lenses.

In this connection, the predetermined condition may be kinds of content, a user preference, or the like. Furthermore, it may be possible to set different positions where the content is displayed depending on the kind of the content or to distribute the content to a user's desired position. Besides, various factors may also be considered.

Meanwhile, the content providing server 100 in accordance with the embodiment includes an additional communication unit 120, a controller 140 and a memory unit 160.

The additional communication unit 120 receives from the route guiding apparatus 200 the user's location detection signal, the activity recognition signal and the bio-signal, and forwards content extracted from the memory unit 160 to the content providing apparatus 200.

The bio-signal of the user is not necessarily received from the content providing apparatus 200, but may be directly received from the bio-signal sensing unit 300.

The controller 140 determines a user's status based on the user's location detection signal and the user's activity recognition signal received through the additional communication unit 120. Here, the user's status includes, e.g., whether the user's location is indoor or outdoor, e.g., a cycle road, a trail, a sidewalk route, a motor road or the like, at what acceleration the user moves, and in what level a vibration occurs to the user.

Further, the controller 140 estimates a biological activity of the user based on the user's location determined using the user's status and the bio-signal of the user and extracts content corresponding to the biological activity, which is estimated, from the memory unit 160.

As described above, since the activity recognition unit 260 of the route guiding apparatus 200 includes the accelerometer sensor 262 and the gyroscope sensor 264, it is possible to sense at what acceleration a user is moving and in what level a vibration occurs to a user, using the sensors.

An example that the controller 140 determines the user's location determined using the user's status determined based on the location detection signal and the activity recognition signal is shown in TABLE 1.

TABLE 1

|  | Acceleration | Vibration |
| --- | --- | --- |
| Sidewalk route | Less than first acceleration | Exceeding first vibration value |
| Cycle road | Equal to or higher than first acceleration | Equal to or less than first vibration |
| Motor road | Equal to or higher than second acceleration | Equal to or less than second vibration value |

In TABLE 1, the first acceleration means the maximum value of acceleration when a normal person moves on a sidewalk route, which has a value smaller than the second acceleration, and the second acceleration means the maximum value of acceleration when a person moves by bicycle. The first vibration value means the minimum value of vibration when a normal person moves on a sidewalk route, which has a value higher than the second vibration value, and the second vibration value means the minimum value of vibration when a person moves by bicycle.

When a person moves in the fastest relatively, at the second acceleration or higher and vibration is least relatively, the vibration value being equal to or less than the second vibration value as illustrated in TABLE 1, it means that a user moves fast so that it is determined that a user is moving on a motor road by vehicle.

Further, when the acceleration is intermittently fast, which is equal to or more than the first acceleration and the vibration is equal to or less than the first vibration value, it means that a user is moving at a moderate speed in a vibrating state, so that it may be determined that a user is moving on a cycle road by bicycle.

Further, when the acceleration is the fastest relatively, which is less than the first acceleration, and the vibration is relatively high, which exceeds the first vibration value, it means that a user is slowly moving in a severe vibrating state, so that it may be determined that a user is moving on a sidewalk route on foot.

However, when the acceleration is less than the first acceleration and the vibration exceeds the first vibration value, a user may not walk on foot but on a trail. As described above, since the controller 140 receives coordinate information of a user through the location detection unit 240, it is possible to determine a user's location correctly depending on whether the vicinity of user's coordinate information is a trail or a sidewalk route.

Further, the controller 140 determines whether a user's location is indoors or outdoors based on the intensity of a receiving signal of the GPS 242 or WPS 244 of the location detection unit 240. Accordingly, when it is determined that the user is located outdoors or outdoors, it may be helpful to catch a correct position of the outdoor user with reference to the TABLE 1.

In other words, when it is sensed that a user is outdoor, the controller 140 determines a user's location in consideration of user's activity characteristics recognized through the activity recognition unit 260 as described above, and when it is sensed that a user is indoor, the controller 140 determines a user's location based on a signal received from the WPS 244.

In this connection, the memory unit 160 stores content which will be provided to the route guiding apparatus 200. Particularly, the memory unit 160 stores health information, weather information, route information, traffic information, news information, or advertisements.

Further, the location of the user may be determined from a mountain trail, a cycle road, a motor road, a sidewalk route, an indoor location or the like, therefore, the memory unit 160 stores detailed map data such as a mountain trail map, a cycle road map, a motor road map, and a sidewalk route map.

Accordingly, when the controller 140 needs to transmit the route information to the content providing apparatus 200, the controller 140 transmits to the content providing apparatus 200 a map corresponding to the determined user's location through the additional communication unit 120.

For example, when it is determined that a user is on a mountain trail, the controller 140 may extract a trail map from the memory unit 160 and transmit relevant map data to the content providing apparatus 200. When it is determined that a user is on a cycle road, the controller 140 may transmit cycle road map data to the content providing apparatus 200.

In the same manner, for example, when it is determined that a user is indoors, the controller 140 may extract an indoor map of a department store, shop, shopping mall, or subway station corresponding to the location of the user from among indoor maps of the memory unit 160 and transmit relevant indoor map data to the route guiding apparatus 200.

The above description has been made to a process to determine the location of the user and transmit content related to the route information to the content providing apparatus 200. Hereinafter, a description will be made on a process to estimate a biological activity of the user and then transmit health information, weather information, traffic information, news information, or advertisement.

As described above, the bio-signal sensing unit 300 includes one or more a heart rate sensor 320, a temperature sensor 340 and a microphone 360. Accordingly, the controller 140 estimates a biological activity what activity the user acts in consideration of the user's location and bio-signal and then selects content to be delivered to the content providing apparatus 200.

TABLE 2 below is an example that a user's location is determined based on a bio-signal sensing value of the bio-signal sensing unit 300.

TABLE 2

|  | Heart rate | Temperature | Breath |
|---|---|---|---|
| Sleeping | Equal to or less than first heart rate | Equal to or less than first body temperature | Regular |
| Sidewalk | Equal to or less than second heart rate | Equal to or less than second body temperature | Regular |
| Running | Exceeding third heart rate | Exceeding third body temperature | Irregular |
| Cycling | Equal to or less than third heart rate | Equal to or less than third body temperature | Irregular |
| Automobile riding | Equal to or less than first heart rate | Equal to or less than first temperature | Regular |

In TABLE 2, the first heart rate means a heart rate when sleeping or no special operation, which has a value less than the second heart rate, the second heart rate means a heart rate when moving on a sidewalk, which has a value less than the third heart rate, and the third heart rate means the maximum heart rate when riding a bicycle.

Further, the first body temperature means a body temperature when sleeping or no special action, which has a value less than the second body temperature, the second body temperature means an increased body temperature when moving on a sidewalk, which has a value less than the third body temperature, and the third body temperature means the maximum body temperature when riding a bicycle.

As described in Table 2, when it is measured that heart rate is the lowest, which is equal to or less than the first heart rate, body temperature is less than the first body temperature, and breath is regular, it is estimated that a user is sleeping indoor or in a vehicle.

Further, when it is measured that heart rate is equal to or less than the second heart rate, body temperature is equal to or less than the second body temperature and breath is regular, it is estimated that a user is moving on a sidewalk on foot. In such a manner, it is possible to determine a user's biological activity such as running, riding a bicycle, riding on a car, or the like.

Especially, when a user is sleeping and is riding a car, user's bio-signals are similarly sensed. However, when referring to the example reviewed in Table 1, it is possible to discriminate whether a user is sleeping indoor or in a vehicle depending a location of the user that is determined although similar bio-signals are sensed.

Consequently, the controller 140 is capable of estimating the biological activity of the user based on the location of the user derived from the TABLE and the bio-signals listed in TABLE 2 and transmit content suitable for the user's biological activity to the content providing apparatus 200.

As described above, the controller 140 is able to transfer content containing health information, weather information, route information, traffic information, news information or advertisement.

First, if it is determined that the user is indoors or it is estimated that the user is sleeping, the controller 140 transfers content such as health information, weather information, route information, traffic information, news information or advertisement.

That is, when the user is indoors, or sleeping, a typical bio-signal may be detected from the user. Therefore, it may be possible to check the health of the user based on such a bio-signal, and the information about the check result may be transferred to the content providing apparatus 200. Meanwhile, when a destination to move outdoors from indoors is set, weather, route and traffic information during a traveling course and transfer news information of the day may be transferred to the content providing apparatus 200.

In particular, in the case where the destination and an expected arrival time to the destination are set in relation to the provision of the route and traffic information, route information and traffic information may be transferred to the content providing apparatus 200 so that the user can reach the destination within the expected arrival time.

In this case, a determination as to whether the expected arrival time is set can be made by receiving information related to the destination and the expected arrival time from the content providing apparatus 200.

Further, because information about the public transport is included in the traffic information and route information, the controller 140 may be transfer information including the traffic information and a departure time of the public transport such as whether to start from which station or subway stop.

In the embodiment of the present invention, the content providing apparatus 200 may be able to cumulatively store a life pattern of a user relating to a leave-time when a user goes out regularly or a destination to which a user moves periodically. Accordingly, the content providing server 100 receives the life pattern and may transfer content including route information to reach the destination in time, traffic information such as a public transport, and a departure time of the public transport based on the life pattern.

Second, if the controller 140 estimates that a user is moving on a sidewalk on foot, it may transmit content such as weather information, route information about a travel on foot, traffic information, advertisement, etc.

That is, when the user is moving on foot, the movement of the user may be affected by weather, and so, the user may do better to receive weather information of the day from the content providing server 100. Further, where a destination is set, route and traffic information to the destination may be transferred to the content providing apparatus 200, and advertisements about restaurants and shops along the route to the destination nearby may also be transferred to the content providing apparatus 200.

When the destination and the expected arrival time to the destination is set concretely, the controller 140 may provide route information to reach the destination within the expected arrival time as described above. However, if determining that it is difficult to reach the destination within an appointed time, the controller may search a public transport around the destination and then transfer the searched result along the route information and weather information in detail until the expected arrival time.

On the other hand, if the destination has not been set, the controller may suggest changing to the public transport for the user or moving into indoors depending on weather of the day, or may also guide a location where to buy necessary goods such as parasols or umbrellas depending on weather of the day.

Further, because the route information may be represented in various forms in accordance with the embodiment of the invention, the route information may be displayed onto the display unit 280 of the content providing apparatus 200, clock or glasses in such a manner as TBT, an augmented reality, and the like.

Additionally, when a user moves to the same path that has been experienced before, a moving speed and location of the earlier of the user along the path may be provided together with the route information to the content providing apparatus 200, which allows the user to compare the moving speed and location of the earlier with a current moving behavior of the user through a screen.

Besides, the advertisements about shops and restaurants around the user to move may also be selectively transferred in conformity with the statistics such as a user's age, gender, hobbies, a cumulative selection list of the user, and the like.

Third, if it is estimated that the user is running, the controller 140 may transmit content such as health information, weather information, route information, and advertisements.

That is, when the user is running, it may be possible to check a health condition of the user based on a heart rate and a body temperature to provide health information. Further, weather information of the day may be transmitted to the content providing apparatus, inclusive of a path up to surrounding places to take a break, advertisements about neighborhood shops or restaurants, and information such as time taken to run, route information, or calorie consumption information.

In particular, if it is revealed that the path to be transmitted is transmitted before, the controller may transfer route information including a moving speed and location of the earlier of the user.

Fourth, if it is estimated that a user is riding a bike, the controller 140 may provide content such as health information, weather information, route information on a bicycle road, advertisements, and the like.

That is, when the user is riding a bicycle, the controller may provide health information by checking a health condition of the user based on a heart rate and a body temperature, transfer weather information of the day may be transmitted, transfer a path up to surrounding places to take a break and advertisements about neighborhood shops or restaurants, and also transmit information such as time taken to ride a bike, route information, or spent calories information. In addition, it may transfer information about a bicycle repair shop placed in a route around the user to move.

When a destination has been set specifically, the controller may provide route information to reach the destination. However, if it is determined that it is difficult to reach the destination within an appointed time, the controller may search a public transport around the destination and transfer the searched public transport along with route information to the destination and provide weather information until an expected arrival time.

In contrast, if a destination has not been set, the controller suggest changing to a public transport or moving into indoor depending on weather of the day and also guide the location where to buy necessary goods such as parasols or umbrellas depending on the weather of the day.

Further, since the route information may be represented in various forms in accordance with the embodiment of the invention, it may be displayed onto the display unit 280 of the content providing apparatus 200, clock or glasses in such a manner as TBT, an augmented reality, and the like.

In addition, when a user moves to the same route that has been experienced before, the controller may transfer a moving speed and location of the earlier of the user along the path may be provided together with the route information to the content providing apparatus 200, which allows the user to compare the moving speed and location of the earlier with a current moving behavior of the user through a screen.

Fifth, if it is estimated that a user is climbing a mountain, the controller 140 provides content such as health information, weather information, route information about mountain trails, and the like.

That is, when the user is mountain climbing, the controller may provide health information by checking a health condition of the user based on a heart rate and a body temperature, transfer weather information such as sunrise and sunset time of the day, and provides a path to climb up to the top or route information to move toilets, rest stops, and a shelter.

When a destination has been set specifically, the controller may estimate an expected descent time of the user in consideration of the sunset time. Therefore, it may provide information to notify it or route information moving to a shelter located near a mountain trail, and specifically transfer weather information until an expected arrival time.

In contrast, when a destination has not been set, the controller may provide a suggestion to move into an indoor place such as a shelter depending on the weather information of the day.

Further, since the route information may be represented in various forms in accordance with the embodiment of the invention, it may be displayed onto the display unit 280 of the content providing apparatus 200, clock or glasses in such a manner as TBT, an augmented reality, and the like.

In addition, when a user moves to the same route that has been experienced before, the controller may transfer a moving speed and location of the earlier of the user along the path may be provided together with the route information to the content providing apparatus 200, which allows the user to compare the moving speed and location of the earlier with a current moving behavior of the user through a screen.

Sixth, if it is estimated that a user is moving in the car, the controller may provide content such as routing information about a motor road, traffic information, news information, advertisements and the like.

In other words, when the user is moving in the car, the controller may provide route information to a destination and traffic information, and transfer news information of the day and advertisements such as shops and restaurants located on the route to the destination.

In particular, when a destination and an expected arrival time in relation to the provision of the route and traffic information has been set, the controller may provide the route and traffic information to the destination while guiding a departure time by estimating a travel time to the destination.

In accordance with to an exemplary embodiment of the present invention, the content providing apparatus 200 may include but not limited to any devices such as smartphones, PNDs (Personal Navigation Devices) or the like, which are capable of providing content with a user.

Figure 2:
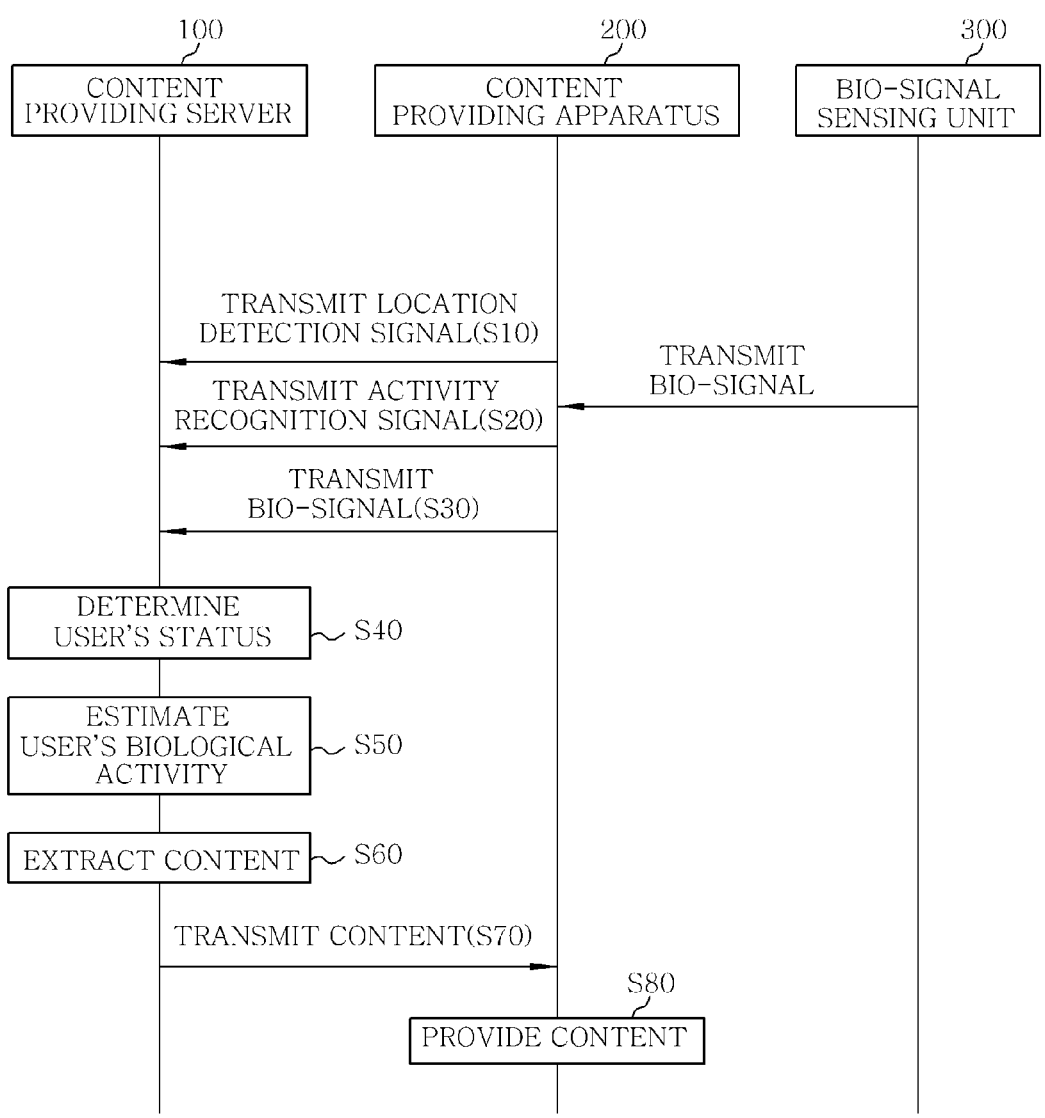
FIG. 2 is a flow chart illustrating a process for providing content in accordance with an embodiment of the present invention.

FIG. 2 is a flow chart illustrating a method for providing content in accordance with an embodiment of the present invention.

Figure 3:
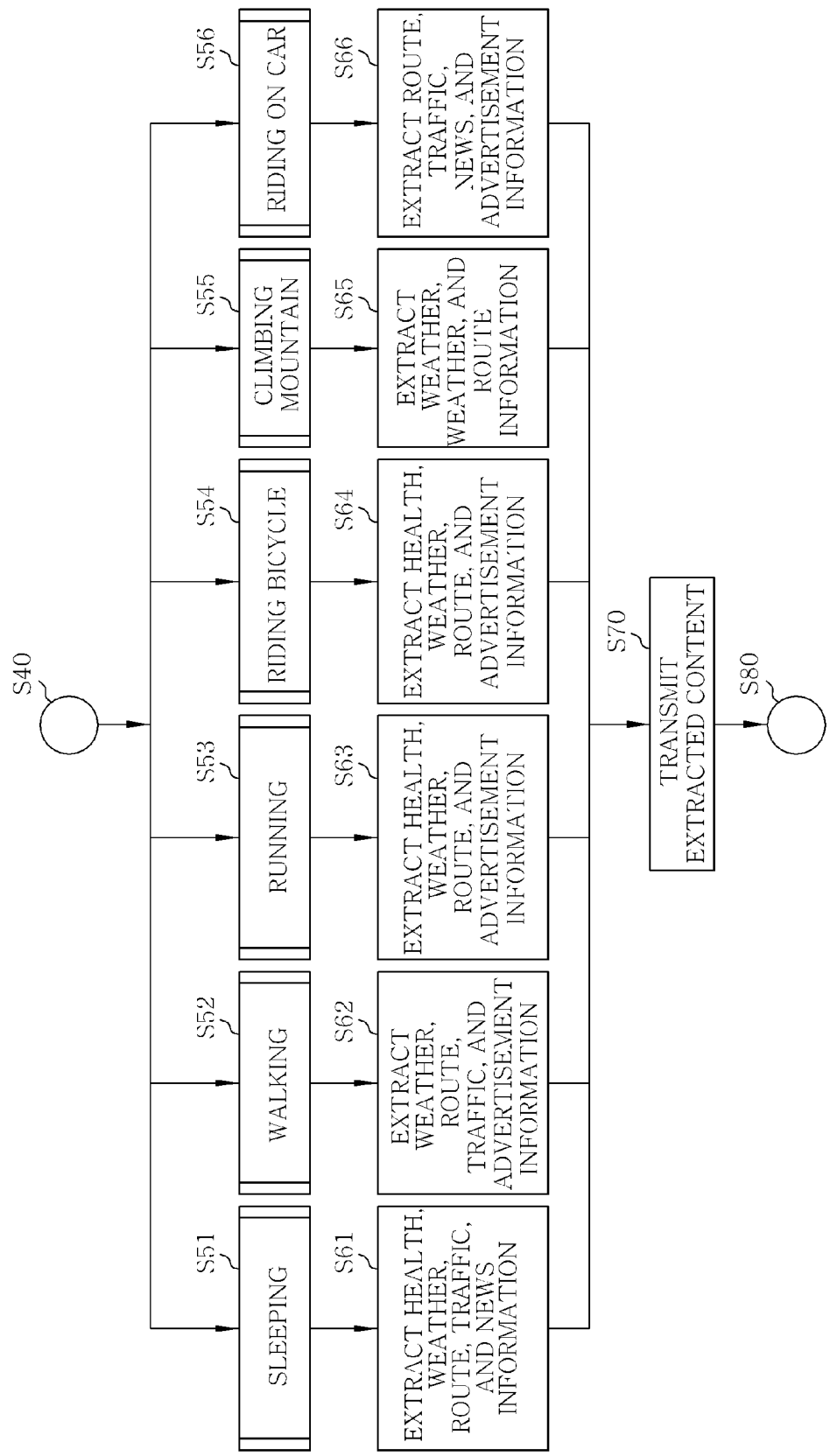
FIG. 3 is a flow chart illustrating a process for extracting content to be sent to a content providing apparatus in accordance with an embodiment of the present invention.

FIG. 3 is a flow chart illustrating a method for extracting content to be sent to a content providing apparatus in accordance with an embodiment of the present invention.

A content providing method in accordance with the embodiment will be described with reference to FIGS. 2 and 3 as follows. First, when a request of providing content is received from a user, the content providing apparatus 200 transmits a location detection signal, which is detected by the location detection unit 240, to the content providing server 100 (Block S10); and an activity recognition signal, which is recognized by the activity recognition unit 260, to content providing server 100 (Block S20).

Further, the content providing apparatus 200 may receive a bio-signal sensed by the bio-signal sensing unit the bio-signal sensing unit 300 and then transmit the received bio-signal to the content providing server 100 (Block S30).

In this case, when transmitting the location detection signal, the activity recognition signal and the bio-signal to the content providing server 100 (Blocks S10 to Block s30), each signal transmission is not limited to the order described above, and it may be possible to transmit each signal in different orders.

Subsequently, the content providing server 100 determines a user's status based on the location detection signal and the activity recognition signal (Block S40) and estimates a biological activity of the user based on the user's location determined using the user's status and the received bio-signal (Block S50).

More specifically, the content providing server 100 extracts coordinate information on which the user is located from the received position detection signal, and corrects the coordinate information based on the received activity recognition signal, thereby determining the location of the user.

That is, since the location information received from GPS satellites includes some errors, the content providing server 100 may determine more precisely the user's location with reference to an activity characteristic or bio-signal of the user.

Determining the user's location is not limited thereto, and other known or unknown different methods may also be employed to determine the user's location.

The process of extracting the content suitable for a biological activity of the user will be described with reference to FIG. 3 as follows. The biological activity estimated in Block S50 may be sleeping, sidewalk, running, cycling, automobile riding, mountain climbing, and the like.

When it is estimated that a user is sleeping (Block S51), the controller 140 of the content providing server 100 extracts content that contains health information, weather information, route information, traffic information, news information and the like (Block S61).

When it is estimated that a user is walking (Block S52), the controller 140 extracts content that contains weather information, route information about a walking trip on foot, traffic information, advertisements and the like (Block S62).

When it is estimated that a user is riding a bicycle (Block S54), the controller 140 extracts content that contains health information, weather information, route information about a bicycle road, advertisements, and the like (Block S64).

When it is estimated that a user is climbing a mountain (Block S55), the controller 140 extracts content that contains health information, weather information, route information about a mountain trail, and the like (Block S65).

When it is estimated that a user is riding in a car (Block S56), the controller 140 extracts content that contains route information about a motor road, traffic information, news information, advertisements, and the like (Block S64).

The details of the content such as the health information, weather information, route information, traffic information, news information, advertisements and the like may be varied and transferred with the location and biological activity of the user.

Thereafter, the content providing server 100 transmits the content corresponding to the user's location determined using the user's status and the biological activity of the user to the content providing apparatus 200 (Block S70), which, in turn, provides the transmitted content to the user (Block S80).

As mentioned above, user's location and bio-activity are sensed, a user's location is correctly extracted, and content necessary for the user is actively provided to the user, thereby increasing a user's convenience and enhancing a feeling of satisfaction.

While the invention has been shown and described with respect to the embodiments, the present invention is not limited thereto. It will be understood by those skilled in the art that various changes and modifications may be made without departing from the scope of the invention as defined in the following claims.

What is claimed is:

1. A method for providing content that is executed by a content providing apparatus including a location detection unit and an activity recognition unit, a content providing server including a controller or a bio-signal sensing unit which is integrally formed with the content providing apparatus or is incorporated in separate devices, the method comprising:
   the content providing apparatus transmitting to the content providing server a user's location detection signal detected by a location detection unit;
   the content providing server receiving the user's location detection signal from the content providing apparatus;
   the content providing apparatus transmitting to the content providing server a user's activity recognition signal recognized by an activity recognition unit;
   the content providing server receiving the user's activity recognition signal from the content providing apparatus;
   the content providing apparatus transmitting a user's bio-signal received from the bio-signal sensing unit to the content providing server;
   the content providing server receiving the user's bio-signal from the content providing apparatus or the bio-signal sensing unit;
   the controller determining a user's status based on the user's location detection signal and the user's activity recognition signal;
   the controller estimating a user's biological activity based on a user's location determined by the user's status, and the user's bio-signal;
   the content providing server transmitting the content corresponding to the user's biological activity to the content providing apparatus;
   the content providing apparatus receiving the content corresponding to the user's biological activity from the content providing server; and
   the content providing apparatus providing the received content,
   wherein the user's location includes at least one of a cycle road, a motor road, and a sidewalk route,
   wherein the user's biological activity includes at least one of sleeping, sidewalk, running, cycling, and automobile riding, and
   wherein the content corresponding to the user's biological activity includes at least one of health information, weather information, route information, traffic information, news information, and advertisements,
   wherein the user's bio-signal includes at least one of a heart rate and a body temperature,
   wherein the user's activity recognition signal includes at least one of an acceleration and a vibration,
   wherein the user's location is determined to be the sidewalk route when the acceleration is less than a pre-determined first acceleration value and the vibration is higher than a pre-determined first vibration value, to be the cycle road when the acceleration is equal to or higher than the pre-determined first acceleration value and less than a pre-determined second acceleration value and the vibration is equal to or less than the pre-determined first vibration value and higher than a pre-determined second vibration value, and to be the motor road when the acceleration is equal to or higher than the pre-determined second acceleration value and the vibration is equal to or less than the pre-determined second vibration value,
   wherein the pre-determined second acceleration value is higher than the predetermined first acceleration value and the pre-determined second vibration value is less than the pre-determined first vibration value,
   wherein the user's biological activity is determined to be the sleeping or the automobile riding when the heart rate is equal to or less than a pre-determined first heart rate value and the body temperature is equal to or less than a pre-determined first body temperature value, to be the sidewalk when the heart rate is higher than the pre-determined first heart rate value and equal to or less than a pre-determined second heart rate value and the body temperature is higher than the pre-determined first body temperature value and equal to or less than a pre-determined second body temperature value, to be the running when the heart rate is higher than a pre-determined third heart rate value and the body temperature is higher than a predetermined third body temperature value, and to be the cycling when the heart rate is higher than the pre-determined second heart rate value and equal to or less than the pre-determined third heart rate value and the body temperature is higher than the pre-determined second body temperature value and equal to or less than the pre-determined third body temperature value, and
   wherein the pre-determined second heart rate value is higher than the pre-determined first heart rate value and less than the pre-determined third heart rate value, and the pre-determined second body temperature value is higher than the pre-determined first body temperature value and less than the pre-determined third body temperature value.

2. The method of claim 1, further comprising:
   when it is determined that the user is indoors or when it is estimated that the biological activity of the user is sleeping, determining whether a destination and an expected arrival time are set; and
   when it is determined that the destination and an estimated arrival time are set, transmitting content including at least one of route information to reach the destination, traffic information and weather information in the course of moving to the destination to the content providing apparatus.

3. The method of claim 1, further comprising:
   when it is determined that the user is indoors or when it is estimated that the biological activity of the user is sleeping, transmitting content including at least one of route information to reach a destination within an expected arrival time, traffic information containing a public transport, and a departure time.

4. The method of claim 1, further comprising:
   when it is estimated that the biological activity of the user is walking on foot or riding on a car, determining whether a destination and an expected arrival time are set; and when it is determined that the destination and the expected arrival time are set, transmitting content including at least one of route information to reach the destination within the expected arrival time and traffic information about a public transport to reach the destination to the content providing apparatus.

5. The method of claim 4, further comprising:
when it is estimated that the biological activity of the user is one of running, riding a bike, or climbing a mountain, transmitting the content providing apparatus content including health information, route information and calorie consumption information to the content providing apparatus, wherein the route information includes a moving speed and location of the earlier of the user.

6. The method of claim 1, further comprising:
when it is estimated that the biological activity of the user is climbing a mountain, transmitting content including route information relating to a shelter located near a mountain trail, in consideration of an expected descent time of the user depending on weather of the day to the content providing apparatus.

7. The method of claim 1, wherein said providing apparatus providing the received content comprises:
transmitting content including at least one of route information to reach a destination within an expected arrival time, traffic information containing a public transport, and a departure time when it is determined that the user is indoors or when it is estimated that the biological activity of the user is sleeping;
determining whether a destination and an expected arrival time are set when it is estimated that the biological activity of the user is walking on foot or riding on a car;
transmitting content including at least one of route information to reach the destination within the expected arrival time and traffic information about a public transport to reach the destination to the content providing apparatus when it is determined that the destination and the expected arrival time are set;
transmitting the content providing apparatus content including health information, route information and calorie consumption information to the content providing apparatus, when it is estimated that the biological activity of the user is one of running, riding a bike, or climbing a mountain, wherein the route information includes a moving speed and location of the earlier of the user; and
transmitting content including route information relating to a shelter located near a mountain trail, in consideration of an expected descent time of the user depending on weather of the day to the content providing apparatus when it is estimated that the biological activity of the user is mountain climbing.

8. An apparatus for providing content, the apparatus comprising:
a location detection unit configured to detect a location of a user to produce a location detection signal;
an activity recognition configured to recognize an activity of the user to produce an activity recognition signal;
a communication unit configured to transmit the location detection signal and the activity recognition signal, receive a bio-signal from a bio-signal sensing unit, and receive content from the content providing server; and
a display unit configured to represent the content,
wherein the user's location includes at least one of a cycle road, a motor road, and a sidewalk route,
wherein the user's biological activity includes at least one of sleeping, sidewalk, running, cycling, and automobile riding, and
wherein the content corresponding to the user's biological activity includes at least one of health information, weather information, route information, traffic information, news information, and advertisements,
wherein the user's bio-signal includes at least one of a heart rate and a body temperature,
wherein the user's activity recognition signal includes at least one of an acceleration and a vibration,
wherein the user's location is determined to be the sidewalk route when the acceleration is less than a pre-determined first acceleration value and the vibration is higher than a pre-determined first vibration value, to be the cycle road when the acceleration is equal to or higher than the pre-determined first acceleration value and less than a pre-determined second acceleration value and the vibration is equal to or less than the pre-determined first vibration value and higher than a pre-determined second vibration value, and to be the motor road when the acceleration is equal to or higher than the pre-determined second acceleration value and the vibration is equal to or less than the pre-determined second vibration value,
wherein the pre-determined second acceleration value is higher than the predetermined first acceleration value and the pre-determined second vibration value is less than the pre-determined first vibration value,
wherein the user's biological activity is determined to be the sleeping or the automobile riding when the heart rate is equal to or less than a pre-determined first heart rate value and the body temperature is equal to or less than a pre-determined first body temperature value, to be the sidewalk when the heart rate is higher than the pre-determined first heart rate value and equal to or less than a pre-determined second heart rate value and the body temperature is higher than the pre-determined first body temperature value and equal to or less than a pre-determined second body temperature value, to be the running when the heart rate is higher than a pre-determined third heart rate value and the body temperature is higher than a predetermined third body temperature value, and to be the cycling when the heart rate is higher than the pre-determined second heart rate value and equal to or less than the pre-determined third heart rate value and the body temperature is higher than the pre-determined second body temperature value and equal to or less than the predetermined third body temperature value, and wherein the pre-determined second heart rate value is higher than the pre-determined first heart rate value and less than the pre-determined third heart rate value, and the pre-determined second body temperature value is higher than the pre-determined first body temperature value and less than the pre-determined third body temperature value.

9. The apparatus of claim 8, wherein the content apparatus comprises one of a navigation system and a smartphone.

10. The apparatus of claim 8, wherein the content providing apparatus further comprises a separate display unit, wherein the separate display unit comprises one of wearable glasses and a wearable watch.

11. The apparatus of claim 10, wherein the glasses is configured to represent the content through a left lens or a right lens of the glasses in accordance with a predetermined condition.

12. The apparatus of claim 10, wherein the glasses is configured to represent the content on an upper, lower, left, or right section of left or right lenses thereof.

13. A server of providing content, the server comprising:
an additional communication unit configured to receive a user's location detection signal, a user's activity recognition signal and a user's biological activity signal;
a memory unit configured to store content to be provided to the content providing apparatus; and
a controller configured to determine a user's status based on the user's location detection signal and the user's activity recognition signal, estimate a user's biological activity based on a user's location determined using the determined user's status and the bio-signal, and extract content corresponding to the estimated user's biological activity from the memory unit to provide the extracted content to the content providing apparatus through the additional communication unit,
wherein the user's location includes at least one of a cycle road, a motor road, and a sidewalk route,
wherein the user's biological activity includes at least one of sleeping, sidewalk, running, cycling, and automobile riding, and
wherein the content corresponding to the user's biological activity includes at least one of health information, weather information, route information, traffic information, news information, and advertisements,
wherein the user's bio-signal includes at least one of a heart rate and a body temperature,
wherein the user's activity recognition signal includes at least one of an acceleration and a vibration,
wherein the user's location is determined to be the sidewalk route when the acceleration is less than a pre-determined first acceleration value and the vibration is higher than a pre-determined first vibration value, to be the cycle road when the acceleration is equal to or higher than the pre-determined first acceleration value and less than a pre-determined second acceleration value and the vibration is equal to or less than the pre-determined first vibration value and higher than a pre-determined second vibration value, and to be the motor road when the acceleration is equal to or higher than the pre-determined second acceleration value and the vibration is equal to or less than the pre-determined second vibration value,
wherein the pre-determined second acceleration value is higher than the pre-determined first acceleration value and the pre-determined second vibration value is less than the pre-determined first vibration value,
wherein the user's biological activity is determined to be the sleeping or the automobile riding when the heart rate is equal to or less than a pre-determined first heart rate value and the body temperature is equal to or less than a pre-determined first body temperature value, to be the sidewalk when the heart rate is higher than the pre-determined first heart rate value and equal to or less than a pre-determined second heart rate value and the body temperature is higher than the pre-determined first body temperature value and equal to or less than a pre-determined second body temperature value, to be the running when the heart rate is higher than a pre-determined third heart rate value and the body temperature is higher than a predetermined third body temperature value, and to be the cycling when the heart rate is higher than the pre-determined second heart rate value and equal to or less than the pre-determined third heart rate value and the body temperature is higher than the pre-determined second body temperature value and equal to or less than the pre-determined third body temperature value, and
wherein the pre-determined second heart rate value is higher than the pre-determined first heart rate value and less than the pre-determined third heart rate value, and the pre-determined second body temperature value is higher than the pre-determined first body temperature value and less than the pre-determined third body temperature value.

* * * * *